United States Patent [19]

Bailey

[11] Patent Number: 5,571,103

[45] Date of Patent: Nov. 5, 1996

[54] METHOD FOR THE FIXATION OF BONE

[76] Inventor: Kirk J. Bailey, 1220 Bittersweet La., Rochester, Ind. 46975

[21] Appl. No.: 324,957

[22] Filed: Oct. 18, 1994

[51] Int. Cl.$^6$ .............................................. A61B 17/72
[52] U.S. Cl. ................................................ 606/62; 606/76
[58] Field of Search ............................... 606/62, 63, 61, 606/72, 54, 59, 55, 56, 57, 58, 64, 73, 74, 76, 105

[56] References Cited

U.S. PATENT DOCUMENTS

| | | | |
|---|---|---|---|
| 4,312,336 | 1/1982 | Danieletto et al. | 606/57 |
| 4,541,422 | 9/1985 | de Zbikowski | 606/59 |
| 4,604,997 | 8/1986 | De Bastiani et al. | 606/59 X |
| 4,641,636 | 2/1987 | Cotrel | 606/61 |
| 4,922,896 | 5/1990 | Agee et al. . | |
| 4,941,481 | 7/1990 | Wageknecht | 606/59 |
| 4,964,861 | 10/1990 | Agee et al. . | |
| 4,978,348 | 12/1990 | Ilizarov | 606/57 |
| 5,021,054 | 6/1991 | Monfardini et al. | 606/54 |
| 5,261,909 | 11/1993 | Sutterlin et al. | 606/61 |
| 5,281,225 | 1/1994 | Vicenzi | 606/62 |
| 5,350,378 | 9/1994 | Cole et al. | 606/57 |

FOREIGN PATENT DOCUMENTS

| | | | |
|---|---|---|---|
| 2559380 | 8/1985 | France | 606/54 |
| 1287868 | 2/1987 | U.S.S.R. | 606/59 |
| WO94/04087 | 3/1994 | WIPO . | |

OTHER PUBLICATIONS

Namba, Robert S. et al. "Biomechanical Effects of Point Configuration in Kirschner–Wire Fixation," *Clinical Orthopaedics and Related Research*, No. 214, Jan. 1987, pp. 19–22.

Jones, Wallace W., "Biomechanics of Small Bone Fixation," *Clinical Orthopaedics and Related Research*, No. 214, Jan. 1987, pp. 11–18.

McCoy, Michael T. et al., "Comparison of Mechanical Performance in Four Types of External Fixators," *Clinical Orthopaedics and Related Research*, No. 180, Nov. 1983, pp. 23–33.

Chao, Ph.D., Edmund Y. S. et al., "The Effect of Rigidity on Fracture Healing in External Fixation," *Clinical Orthopaedics and Related Research*, No. 241, Apr. 1989, pp. 24–35.

Lewis, Jr., Royce C. et al., "Expandable Intramedullary Device for Treatment of Fractures in the Hand," *Clinical Orthopaedics and Related Research*, No. 214, Jan. 1987, pp. 85–92.

Sisk, T. David, "External Fixation, Historic Review, Advantages, Disadvantages, Complications and Indications," *Clinical Orthopaedics and Related Research*, No. 180, Nov. 1983, pp. 15–22.

Vidal, Jacques, "External Fixation, Yesterday, Today, and Tomorrow," *Clinical Orthopaedics and Related Research*, No. 180, Nov. 1983, pp. 7–14.

Cooney, W. P., "External Fixation of Distal Radial Fractures," *Clinical Orthopaedics and Related Research*, No. 180, November 1983, pp. 44–49.

Peltier, Leonard F., "Fractures of the Distal End of the Radius, An Historical Account," *Clinical Orthopaedics and Related Research*, No. 187, Jul./Aug., 1984, pp. 18–22.

(List continued on next page.)

*Primary Examiner*—Michael Powell Buiz
*Assistant Examiner*—Guy V. Tucker
*Attorney, Agent, or Firm*—Harness, Dickey & Pierce, P.L.C.

[57] ABSTRACT

An apparatus for fixation of a fractured bone. The apparatus includes a first elongation member that is able to at least partially be inserted into two portions of the bone, as well as a second elongated member that is operable to also be partially inserted into the two portions of the bone. The first and second elongated members include an abrasive surface that is able to resist relative rotation between elongated members and a fixation clamp to which the locking members are secured.

11 Claims, 3 Drawing Sheets

OTHER PUBLICATIONS

Podolsky, Anatol et al., "Mechanical Performance of Ilizarov circular External Fixators in Comparison With Other External Fixators," *Clinical Orthopaedics and Related Research,* No. 293, Aug. 1993, pp. 61–70.

Behrens, Fred, "A Primer of Fixator Devices and Configurations," *Clinical Orthopaedics and Related Research,* No. 241, Apr. 1989, pp. 5–14.

Schuind, Frederic et al., "Small External Fixation Devices for the Hand and Wrist," *Clinical Orthopaedics and Related Research,* No. 293, Aug. 1993, pp. 77–82.

Hipporcrates, "The Classic, An Abridged Report on External Skeletal Fixation," *Clinical Orthopaedics and Related Research,* pp. 3–4.

Behrens, Fred, "General Theory and Principles of External Fixation," *Clinical Orthopaedics and Related Research,* No. 241, Apr. 1989, pp. 15–23.

Pettine, Kenneth A. et al., "Analysis of the External Fixator Pin–Bone Interface," *Clinical Orthopaedics and Related Research,* No. 293, Aug. 1993, pp. 18–27.

Sisk, T. David, "General Principles and Techniques of External Skeletal Fixation," *Clinical Orthopaedics and Related Research,* No. 180, Nov. 1983, pp. 96–100.

Chao, Edmund Y. S., et al., "Editorial Comment," *Clinical Orthopaedics and Related Research,* No. 293, 1993, p. 2.

Ulson, H. J. R., "Colles's Fractures: Combined Internal and External Fixation," *Fractures of the Hand and the Wrist,* vol. 4, pp. 276–289.

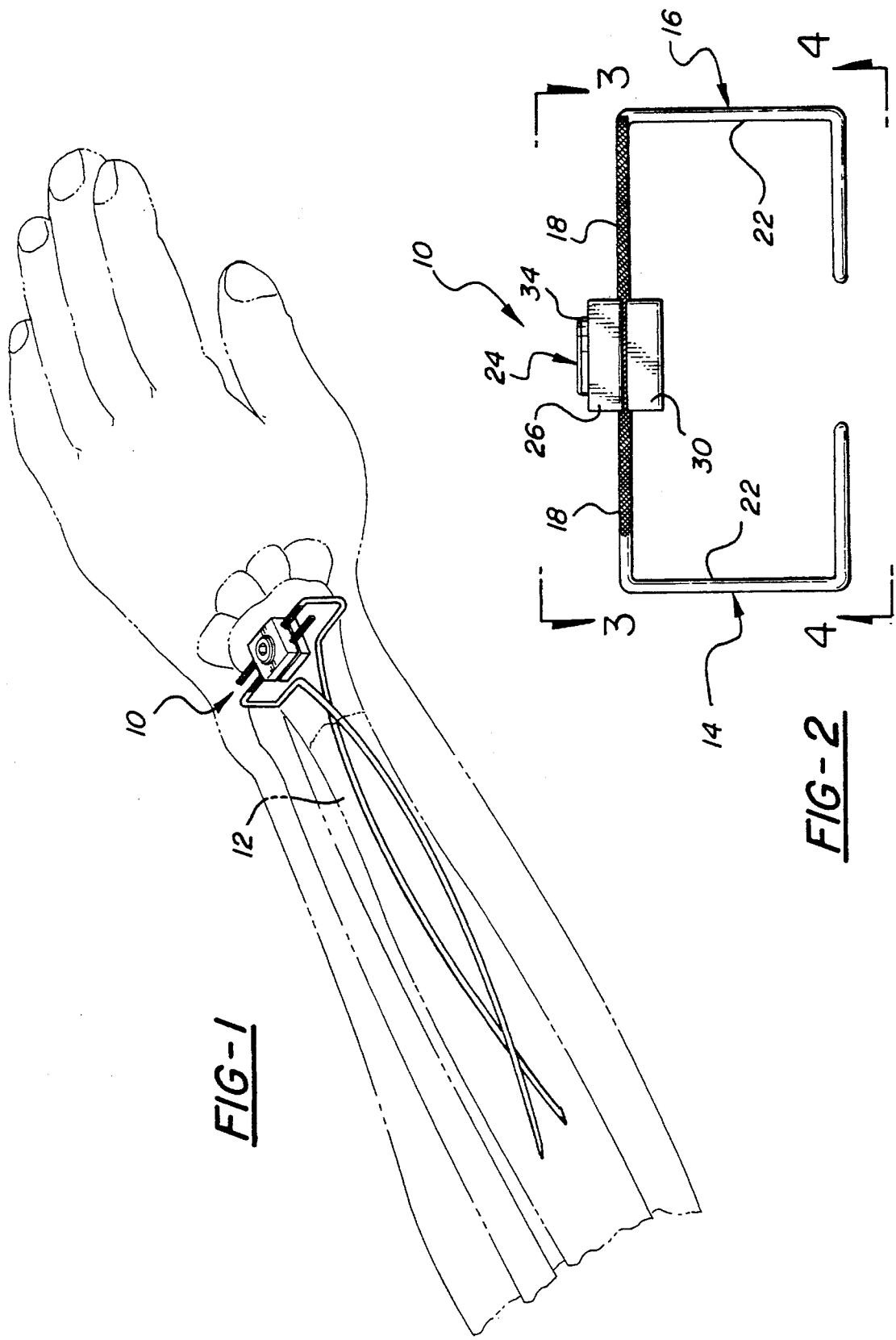

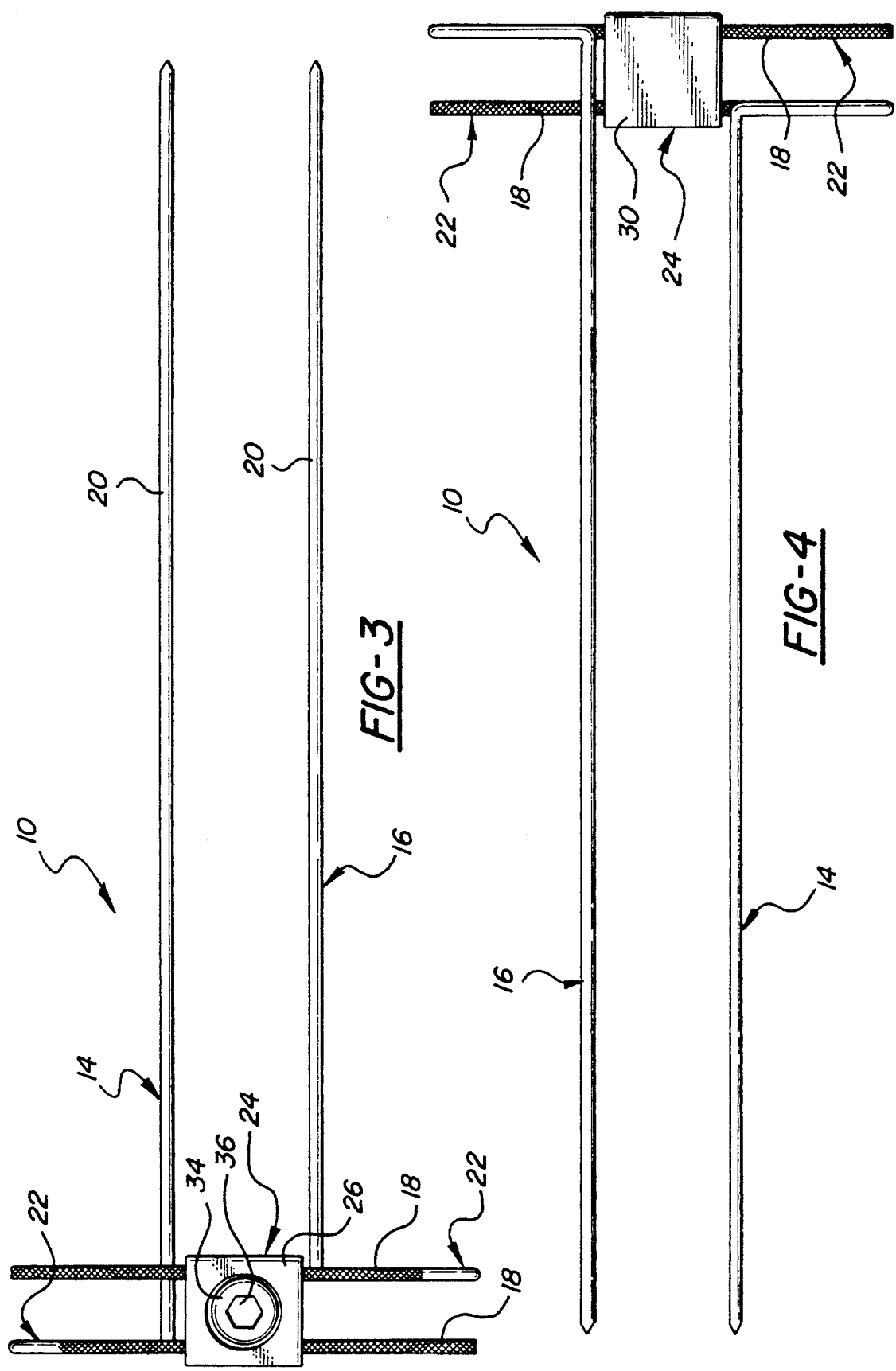

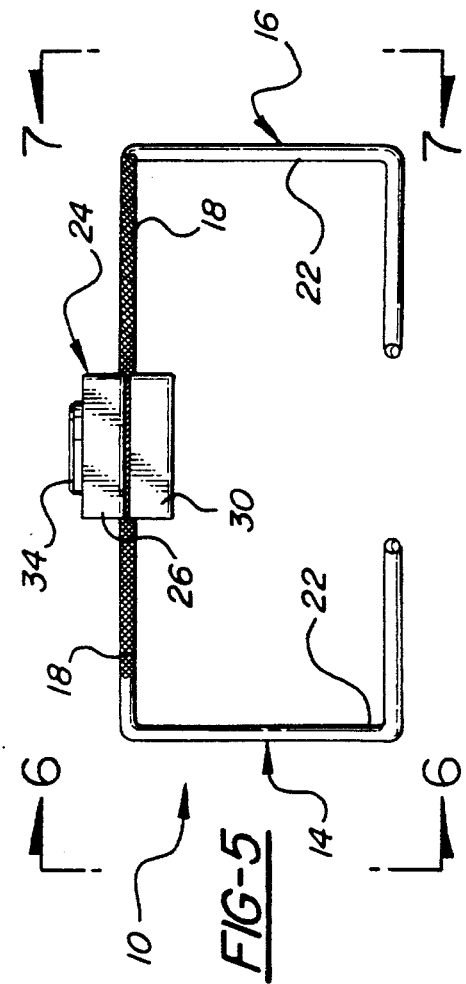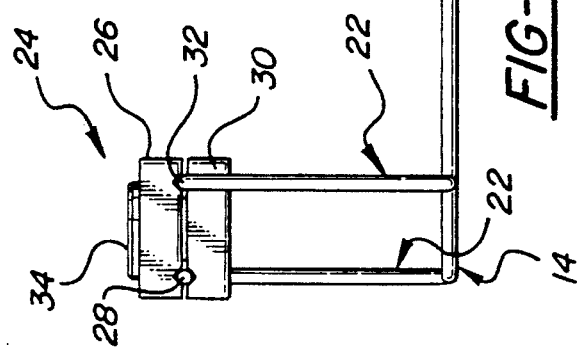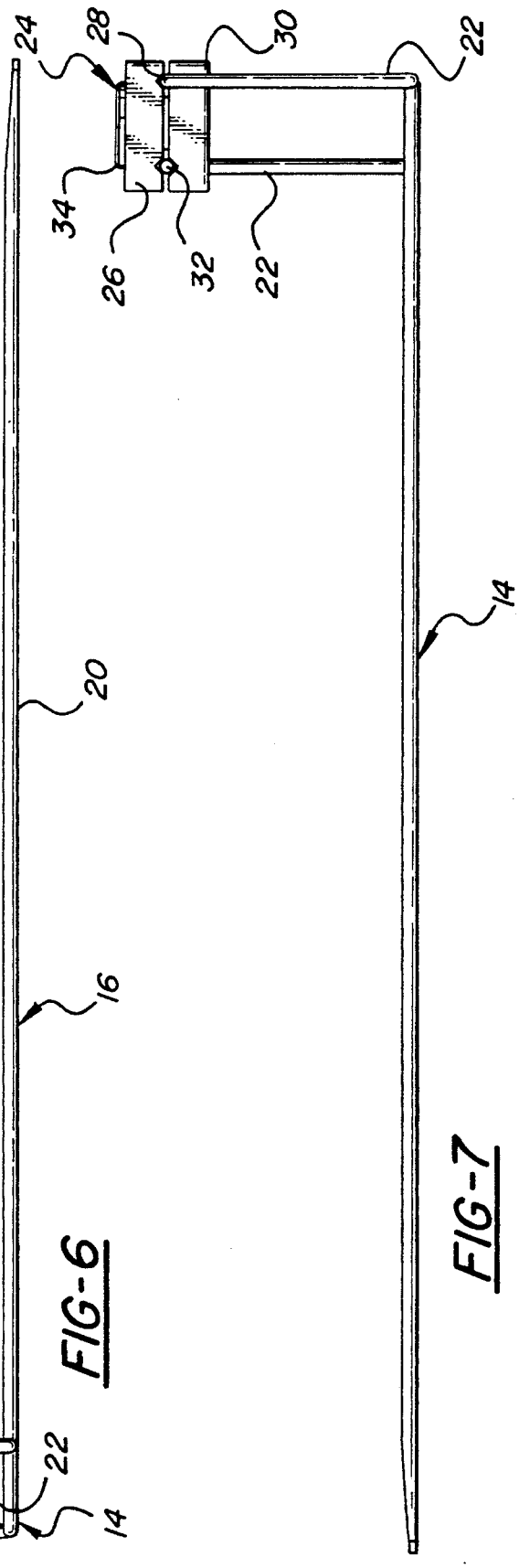

METHOD FOR THE FIXATION OF BONE

BACKGROUND OF THE INVENTION

1. Field of the Invention

This invention relates to fixation devices for stabilizing two portions of bone, and more particularly to a method and apparatus for the fixation of bone fractures.

2. Description of the Related Art

Repairs of fractures of the distal radius and other small bones of the hand, wrist, and distal forearm often present particular difficulties. Fracture of the distal radius, often referred to by eponyms such as Colles' fractures, Smith's fracture, or Barton's fracture (herein referred to as Colles' fracture), are commonly unstable and may involve complications such as avulsion of the ulnar styloid, tearing of the collateral ulnar ligament, marked displacement of bone fragments from the distal radius or ulna, or derangement of the distal radioulnar joint. Injury to the nearby median nerve by bone spicules may result in sensory and motor paralysis. Persistent compression of the ulnar nerve creates symptoms of carpal tunnel syndrome, which may require operative diversion of the volar carpal ligament for relief.

There are two general types of devices which may be used to achieve fixation and, therefore, repair of a Colles' fracture. These devices are generally referred to as external fixation devices and internal fixation devices. External fixation devices are those devices that stabilize a fracture through direct penetration of percutaneous pins into bone and anchorage of the pins to external devices. In contrast, internal fixation devices are those devices that are located completely internal to the body. External fixation devices present several key advantages over internal fixation devices, including simplicity of the operative procedure and minimal disturbance of the bone biology, and decreased risk of deep infection and subsequent nonunion. External fixation is particularly indicated in cases of bone loss to preserve skeletal length.

Techniques of closed reduction and external immobilization using external fixation devices have been advocated for repair of Colles' fractures. Such unstable fractures of the distal radius may be treated with small external fixators with pins implanted in the distal radial epiphysis to allow for early wrist joint mobility. Such external fixation devices are particular advantageous in allowing skeletal distraction and preservation of bone alignment and bone length.

A variety of small external fixators are currently available for application of external fixation principles to small bones, such as the hand and wrist. Brazilian Patent No. 62 00 124 U discloses an external fixation device having percutaneous intramedullary pins and an external clamp with a fixator coupling device for stabilization of distal fractures of the radius, including those defined as Colles' fractures. This device is designed to prevent migration of the frame structure and to promote rotational stability. Because the fixation pins have a smooth surface, however, rotational stability of the pins in relation to the fixator coupling device is not insured. Additionally, because the fixator coupling device has cylindrical attachment grooves to receive the cylindrical ends of the pins to the fixator coupling device, rotational forces are largely unopposed, allowing potential rotation of the pins with resulting instability of the device. Rotational instability is especially likely with this device during the healing process when adjacent muscles and tendons are in use.

Furthermore, the device disclosed in Brazilian Patent No. 62 00 124 U is constructed from a radiodense substance which does not allow easy verification by X-ray of bone alignment during the course of stabilization and healing of the fracture. Additionally, the external clamp of the fixator coupling device is large and bulky, making trauma to the device more likely and subsequent disruption of bone union. The bulkiness of the clamp also makes the desired use of the associated muscles, tendons, and joints during the healing process less likely.

SUMMARY OF THE INVENTION

In the preferred embodiment, the present invention relates to a method and apparatus for fixation of bone of the distal forearm, hand and wrist after fracture. The device of the present invention is especially useful for stabilization of fractured bones of the distal radius, often called Colles' fractures. Fractures of the distal radius are commonly unstable fractures that must be stabilized in a manner such that reduction of the fracture is maintained at the same time that early use of the associated muscles, tendons, and joints is allowed to prevent atrophy and stiffness.

The device of the present invention includes a first elongation member that is operable to be at least partially inserted to a first and second portion of bone and a second elongation member that is operable to be at least partially inserted to a first and second portion of bone. The apparatus further includes a fixation clamp for securing the first elongation member to the second elongated member. In addition, the apparatus also includes an abrasive surface on a portion of the first elongated member and on a portion of the second elongated member. The abrasive surfaces are operable to resist relative rotation between the fixation clamp and the first and second elongated members. Rotational stability is promoted by these abrasive surfaces, and migration of the device is reduced.

The first and second elongated members may each include a tapered portion for insertion into bone and an untapered portion that protrudes from the skin when the tapered portion is inserted into bone. The tapered portions of the elongated members allow ease of insertion of the elongated members into the fractured area of bone. The untapered portions of the first and second elongated members that protrude from the skin are secured to one another by a fixation clamp for securing the first and the second elongated members together. The fixation clamp may have upper and lower locking members which may each include angled grooves to receive the untapered portions of the elongated fixation members that are above the surface of the skin. The fixation clamp may also induce a screw for compression of the upper locking member against the lower locking member after portions of the untapered portions of the first elongated member and the second elongated member are placed within the angled grooves. The angled grooves of the first and second locking members firmly secure the untapered portions of the elongated members as the fixation clamp is tightened. The angled apertures of the first and second locking members and the abrasive surface of the elongated members increase the resistance to rotation of the untapered portions of the elongated members within the fixation clamp so that relatively smaller locking members can be utilized. The fixation clamp may also be constructed of radiolucent material to allow visualization of fracture reduction throughout the healing process.

Accordingly, an advantage of the present invention is to provide a method and apparatus for the fixation of bone following fracture of the distal forearm, wrist, or hand in which the fractured bones are stabilized in a reduced position by two elongated members that are each anchored to external means for securing the elongated members.

Another advantage of the present invention is to provide a method and apparatus for fixation of bone which reduces the possibility of rotation between the elongating members. In this regard, the present invention includes the abrasive surfaces on a portion of the elongated members, the angled receiving grooves of the locking members, and the fixation clamp to securely anchor the elongated members to the locking members and within the reduced and fixed bones.

A further advantage of the present invention is to provide a method and apparatus for the fixation of bone which is at least partially radiolucent to facilitate visualization of fracture reduction and placement of the apparatus throughout the healing process. Such visualization will allow readjustment of the apparatus if necessary as the fracture heals and as the patient uses the associated muscles, tendons, and joints to prevent atrophy and stiffness.

A further advantage of the present invention is to provide a smaller fixation clamp, and therefore, a smaller apparatus for patient convenience, for encouragement in use of associated muscles, tendons, and joints to prevent atrophy and stiffness, and for minimization of secondary trauma that could result in disruption of bone union.

Accordingly, the present solves the prolbems which existed with the other external fixator described above in the ability to allow x-ray verification of bone alignment during surgery. In addition, the present invention also solves the problems which existed with the other external fixator described above in the ability to achieve rotational stability of the pins.

BRIEF DESCRIPTION OF THE DRAWINGS

Various advantages of the present invention will become apparent to one skilled in the art upon reading the following specification and reference to the following drawings in which:

FIG. 1 is a view of the device for fixation of bone of the distal forearm, hand, and wrist after fracture shown in operative association with a fractured distal radius;

FIG. 2 is an enlarged frontal view of the apparatus for fixation of bone according to the preferred embodiment of the present invention;

FIG. 3 is a top elevational view of the apparatus for fixation of bone according to the preferred embodiment of the present invention taken in the direction of line 3—3 in FIG. 2;

FIG. 4 is a bottom elevational view of the apparatus for fixation of bone according to the preferred embodiment of the present invention taken in the direction of lines 4—4 in FIG. 2;

FIG. 5 is an elevational end view of the apparatus for fixation of bone according to the preferred embodiment of the present invention;

FIG. 6 is a side elevational view of the apparatus for fixation of bone according to the preferred embodiment of the present invention taken in the direction of line 6—6 in FIG. 5; and FIG. 7 is a side elevational view of the apparatus for fixation of bone according to the preferred embodiment of the present invention taken along 7—7 in FIG. 6.

DISCUSSION OF THE PREFERRED EMBODIMENTS

The following discussion of the preferred embodiment of the present invention is merely exemplary in nature. Accordingly, the discussion is in no way intended to limit the scope of the invention, the application of the invention, or the use of the invention.

Referring to FIG. 1, an apparatus 10 for fixation of a bone 12 of the distal forearm, hand, and wrist after fracture is shown. The apparatus 10 may be used for stabilizing a fracture of the distal radius, including those known as Colles' fracture. In particular, the apparatus 10 may be used for percutaneous internal intramedullary stabilization and external fixation of a fracture of the distal radius. As will be appreciated by those skilled in the art, the apparatus 10 may be used in a variety of orthopedic procedures. In particular, the apparatus 10 may be used in procedures where it is desirable to securely fixate adjacent portions of bone.

The apparatus 10 according to the preferred embodiment will now be described in further detail with reference to FIG. 2. To provide stability through percutaneous internal intramedullary fixation, the apparatus 10 includes two elongated members 14 and 16. The first elongated member 14 is operable to be at least partially inserted into the first and second portions of fractured bone 12, while the second elongated member 16 is also operable to be at least partially inserted into the first and second portions of fractured bone 12. Each of the elongated members 14 and 16 has an abrasive surface 18. The abrasive surface is operable to resist relative rotation between each of the elongated members 14 and 16 and a means for securing the first elongated member to the second elongated member discussed below. The abrasive surfaces 18 on each of the elongated members 14 and 16 are formed by a 30 grit blast, though other suitable methods may be used for forming the abrasive surfaces. Each of the elongated members 14 and 16 has a tapered portion 20 for insertion into the fractured bone portions for intramedullary fixation of the bone portions, as well as an untapered portion 22 for stabilization of the portions of the elongated members 14 and 16 external to the skin. A low-speed, high-torque power drill may be used to prepare holes in the bone for insertion of the elongation members 14 and 16.

The first and second elongated members 14 and 16 are each initially formed (i.e., before being bent in the manner shown in FIGS. 1–7) from a wire which is approximately 12.5 inches in length and which has an end portion with a taper of approximately 2 degrees from horizontal. However, a wire having shorter lengths may also be used to form the first and second elongated members 14 and 16. In addition, the tapered portion 20 of the first and second elongated members 14 and 16 is also approximately 0.078" in diameter and has a radius on the tip of approximately 0.015 radians. Finally, when viewed in a manner similar to that shown in FIG. 3 and 4, the tapered portion 20 has peripheral portions which converge at an angle of approximately 60 degrees. The untapered portion 22 of the first and second elongated members 14 and 16 extends laterally approximately 0.8" from the tapered portion 20 and then vertically by approximately 1.0". The untapered portion 22 then extends again laterally approximately 2.5". The first and second elongated members 14 and 16 are preferably formed from 316 LBM stainless steel, though other suitable materials may be used.

To provide means for securing the first elongated member 14 to the second elongated member 16 and to provide stability of the reduced fractured bone 12, the apparatus 10 further includes a fixation clamp 24. The fixation clamp 24 may include an upper locking member 26 with parallel angled grooves 28 for containing portions of the elongated members 14 and 16 external to the skin. In addition, the fixation clamp 24 may also include a lower locking member 30 also with parallel angled grooves 32 for containing portions of the elongated members 14 and 16 external to the skin. One of the elongated members 14 and 16 may be held within one of the parallel angled grooves 28 and 32 and the other of the elongated members 14 and 16 may be held within the other of the parallel angled grooves 28 and 32 on each of the locking members 26 and 30. That is, the upper and lower locking members 26 and 30 may be placed so that the elongated members 14 and 16 lie between the locking members 26 and 30, each within its angled groove. The upper and lower locking members 26 and 30 are preferably 0.6" in width, 1.56" in height and 0.18" in thickness. In addition, while the upper and lower locking members 26 and 30 are preferably made from the polyetherimide resin ULTEM, other suitable materials may be used.

The fixation clamp 24 may also include a screw 34 for compressing the upper locking member 26 against the lower locking member 30 as the screw is turned. The upper and lower locking members 26 and 30 may contain a central cylindrical aperture (not shown) with threads (not shown) for receiving the screw 34. By causing the upper and lower locking members 26 and 30 to be compressed against one another with the external portions of the elongated members 14 and 16 held between the locking members 26 and 30, the elongated members 14 and 16 are securely anchored and the bone 12 is externally fixed in place. The screw 34 includes an aperture 36 for receiving a hex-headed wrench which may be used to rotate the screw.

The head of the screw 34 is preferably sufficiently wide so as to locate a portion of the head of the screw 34 directly above the untapered portions 22 which are located within the grooves 28 and 32. By locating the head of the screw 34 in this manner, the portions of the locking members 26 and 30 directly between the head of the screw 34 and the untapered portions 22 of the first and second elongated members 14 and 16 are only in compression. That is, there is substantially no moment arm extending between the head of a screw 34 and the untapered portions 22 of the first and second elongated members 14 and 16. Since there is substantially no moment arm between the head of the screw 34 and the untapered portions 22, there is less risk of cracking the Ultem which forms the upper and lower locking members 26 and 30 during usage of the apparatus 10.

In addition, the head of the screw 34 is preferably formed from 6061 aluminum and is relatively thin (i.e., preferably approximately 2 millimeters). Because relatively thin aluminum is radiolucent, a surgeon is able to view the fracture through the head of the screw 34. It will be appreciated, however, that other suitable materials may be used to form the screw 34 which are radiolucent at relatively small thicknesses.

The apparatus 10 is preferably inserted into the bone 12 so as to be located in the manner shown in FIG. 1. In this regard, it will be noted that each of the elongated members 14 and 16 are inserted in the bone 12 such that there is three point fixation. That is, each end of the elongated members 14 and 16 are adjacent to calcar bone. In addition, the middle portion of the first and second elongated members 14 and 16 are located on a region of the calcar bone which is on the opposite side of the bone from where the corresponding ends reside as shown in FIG. 1. By inserting the first and second elongated members 14 and 16 in this manner, there is an enhanced resistance to having the portions of the bone 12 separate while the apparatus 10 has been implanted.

Those skilled in the art can now appreciate from the foregoing that the broad teachings of the present invention can be implemented in a variety of forms. Therefore, while the invention was described in connection with particular examples hereof, the true scope of the invention should not be so limited. For example, the present invention may be used with a variety of surgical procedures which may not necessarily involve orthopedic procedures. In addition, the components of device do not necessarily have to be identical to the configuration shown in FIG. 1, but may be of other shapes which are desirable for a particular application. Other modifications will become apparent to those skilled in the art.

What is claimed is:

1. A method for the fixation of at least a first and a second portion of a fractured bone having an intramedullary canal, said method comprising the steps of:

providing a first elongated member that is operable to be at least partially inserted into the first and second portions of the bone;

forming an abrasive surface to at least part of said first elongated member;

providing a second elongated member that is operable to be at least partially inserted into the first and second portions of the bone;

forming an abrasive surface to at least part of said second elongated member;

inserting said first and second elongated members into the intramedullary canal and across the fracture of the first and second portions of the bone; and releasably securing said first elongated member to said second elongated member by engaging the abrasive surfaces in a manner to resist relative rotation between said first and second elongated members.

2. The method for the fixation of at least two portions of a fractured bone as set forth in claim 1, wherein said step of providing a first elongated member further includes the step of forming a substantially right angle bend on said first elongated member.

3. The method for the fixation of at least two portions of a fractured bone as set forth in claim 1, wherein said step of providing a first elongated member further includes the step of forming a substantially smooth surface on said first elongated member for insertion into the intramedullary canal.

4. The method for the fixation of at least two portions of a fractured bone as set forth in claim 1, further comprising the step of providing means to secure said first and second elongated members together.

5. The method for the fixation of at least a first and second portion a fractured of bone as set forth in claim 4, wherein said step of providing means to secure said first and second elongated members together further includes the step of providing a first and second locking member.

6. The method for the fixation of at least a first and a second portion of a fractured bone as set forth in claim 5, wherein said step of providing said first and second locking members further includes the step of forming at least one angled groove in said first locking member.

7. The method for the fixation of at least two portions of a fractured bone as set forth in claim 6, wherein said step of providing said first and second locking members further includes the step of forming at least one angled groove in said second locking member.

8. The method for the fixation of at least two portions of a fractured bone as set forth in claim 7, wherein said step of providing said first and second locking members includes the step of forming said locking members from a polyetherimide resin.

9. The method for the fixation of at least two portions of a fractured bone as set forth in claim 8, wherein the step of securing said first and second elongated members includes the step of causing a screw to engage said first and second locking members.

10. The method for the fixation of at least a first and second portion of a fractured bone as set forth in claim 4, wherein said step of providing said means to secure said first and second elongated members further includes the step of providing radiolucent means for securing said first and second members together.

11. The method for the fixation of at least a first and a second portion of a fractured bone as set forth in claim 1, wherein the step of providing a first elongated member includes the step of providing a tapered portion on said first elongated member for insertion into the bone.

* * * * *